United States Patent [19]

Anner et al.

[11] 4,192,802

[45] Mar. 11, 1980

[54] PROCESS FOR THE MANUFACTURE OF STEROID CARBOXYLIC ACID LACTONES

[75] Inventors: Georg Anner, Basel; Hansuli Wehrli, Reinach, both of Switzerland

[73] Assignee: Ciba-Geigy Corporation, Ardsley, N.Y.

[21] Appl. No.: 926,357

[22] Filed: Jul. 20, 1978

Related U.S. Application Data

[63] Continuation of Ser. No. 791,438, Apr. 27, 1977, abandoned, which is a continuation of Ser. No. 694,275, Jun. 9, 1976, abandoned.

[51] Int. Cl.$^2$ .............................................. C07J 71/00
[52] U.S. Cl. ...................... 260/239.57; 260/239.55 C; 260/397.5
[58] Field of Search ................................. 260/239.57

[56] References Cited

U.S. PATENT DOCUMENTS

| | | | |
|---|---|---|---|
| 3,413,289 | 11/1968 | Gal et al. | 260/239.55 |
| 3,492,292 | 1/1970 | Gal et al. | 260/239.55 |
| 3,738,983 | 6/1973 | Dreyden, Jr. et al. | 260/239.57 |
| 3,847,906 | 11/1974 | Radscheit et al. | 260/239.55 C |
| 3,883,512 | 5/1975 | Stache et al. | 260/239.57 |

FOREIGN PATENT DOCUMENTS 511M 5/1961 France .............................. 260/239.57

*Primary Examiner*—Elbert L. Roberts
*Attorney, Agent, or Firm*—Theodore O. Groeger

[57] ABSTRACT

An advantageous method for the manufacture of steroidal lactones of the spironolactone and canrenone type involves the following reaction sequence: bromination of a 3$\beta$,17-dihydroxy-17$\alpha$-pregn-5-en-21-carboxaldehyde in basic or neutral medium, oxidation of the 5,6-dibromo compound with hexavalent chromium compounds under basic or neutral conditions, dehydrobromination with inorganic basic agents, such as lithium halides in the presence of lithium carbonate, or with organic bases, such as pyridine, oxidation of the steroid-4,6-diene compound so obtained having in the 17-position the same substituents as the starting material mentioned, with compounds of hexavalent chromium in acid solution, optionally after pretreatment with an acid or, in particular, with a thiocarboxylic acid (to introduce the 7$\alpha$-acylthio group, e.g. if spironolactone is to be manufactured). The new process gives better yields than those hitherto described.

20 Claims, No Drawings

PROCESS FOR THE MANUFACTURE OF STEROID CARBOXYLIC ACID LACTONES

CROSS-REFERENCE TO RELATED APPLICATIONS

This application is a continuation of copending application Ser. No. 791,438, filed Apr. 27, 1977, now abandoned which in turn is a continuation of application Ser. No. 694,275, filed June 9, 1976 (now abandoned).

The present invention provides a process for the manufacture of steroid carboxylic acid lactones, in particular of 3-oxo-17α-pregn-4-ene-21,17-carboxylic acid lactones of the formula

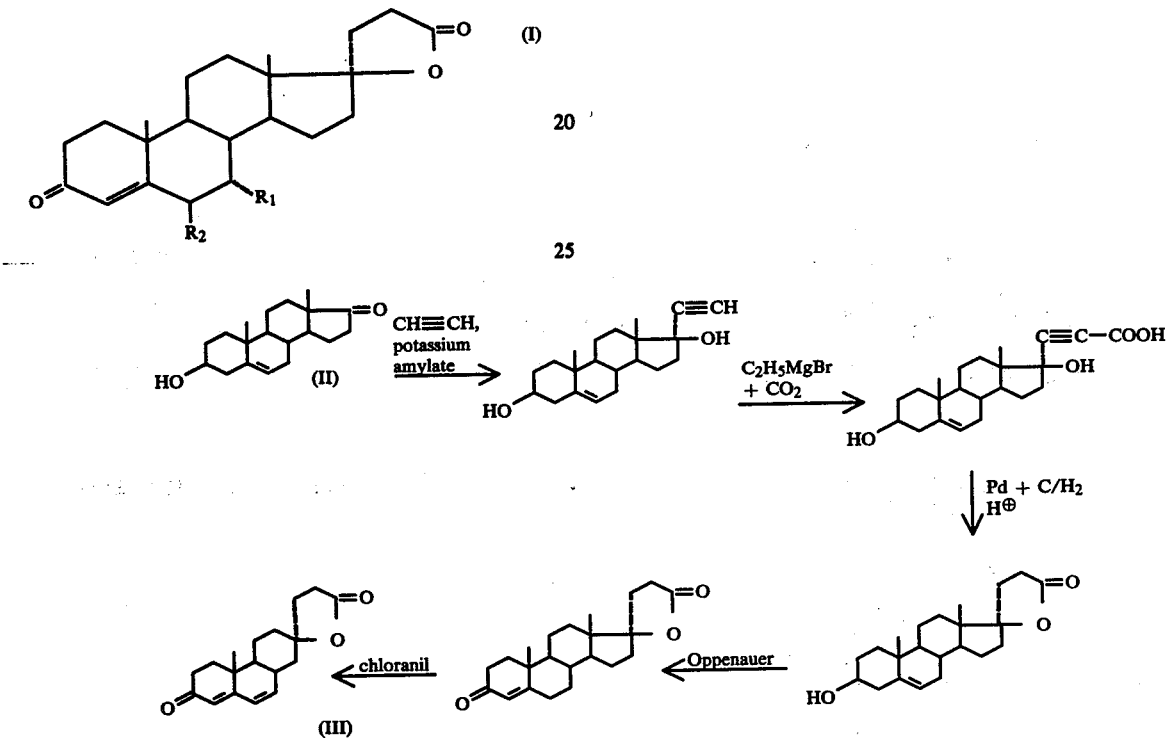

wherein $R_1$ represents an α-acylthio group and $R_2$ represents hydrogen or $R_1$ and $R_2$ together represent a further 6,7-carbon-carbon bond. The acylthio group is in particular a lower acylthio group, primarily the acetylthio group.

The compounds are known aldosterone antagonists, such as spironolactone, the compound of formula I, wherein $R_1$ represents the acetylthio group, which is commercially obtainable under the registered tradename Aldacton A. The 17-hydroxy-21-carboxylic acids and salts thereof which are derived from the $\Delta^{4,6}$ compounds of the above formula also have the same anti-aldosterone effects and are likewise used as aldosterone antagonists.

Numerous processes for obtaining compounds of the formula (I) have been proposed in the literature and patent literature. For example, the Journal of the American Chemical Society, 79, page 4808 and U.S. Pat. No. 2,705,712 describe a process for obtaining a compound of the formula (I), wherein $R_1$ and $R_2$ together represent a further 6,7-carbon-carbon bond, which process can be illustrated as follows (process A):

To obtain the corresponding compounds, wherein R represents an acylthio group, especially the acetylthio group, the above compound (III) is reacted with a thiocarboxylic acid, in particular thioacetic acid, according to the process described in German Pat. No. 1,121,610.

The above process for obtaining the 4,6-diene compound of formula (III) must be regarded as redundant at present because of the unsatisfactory yields. A better alternative is, for example, the process of U.S. Pat. Nos. 3,738,983 and 3,270,008 (process B):

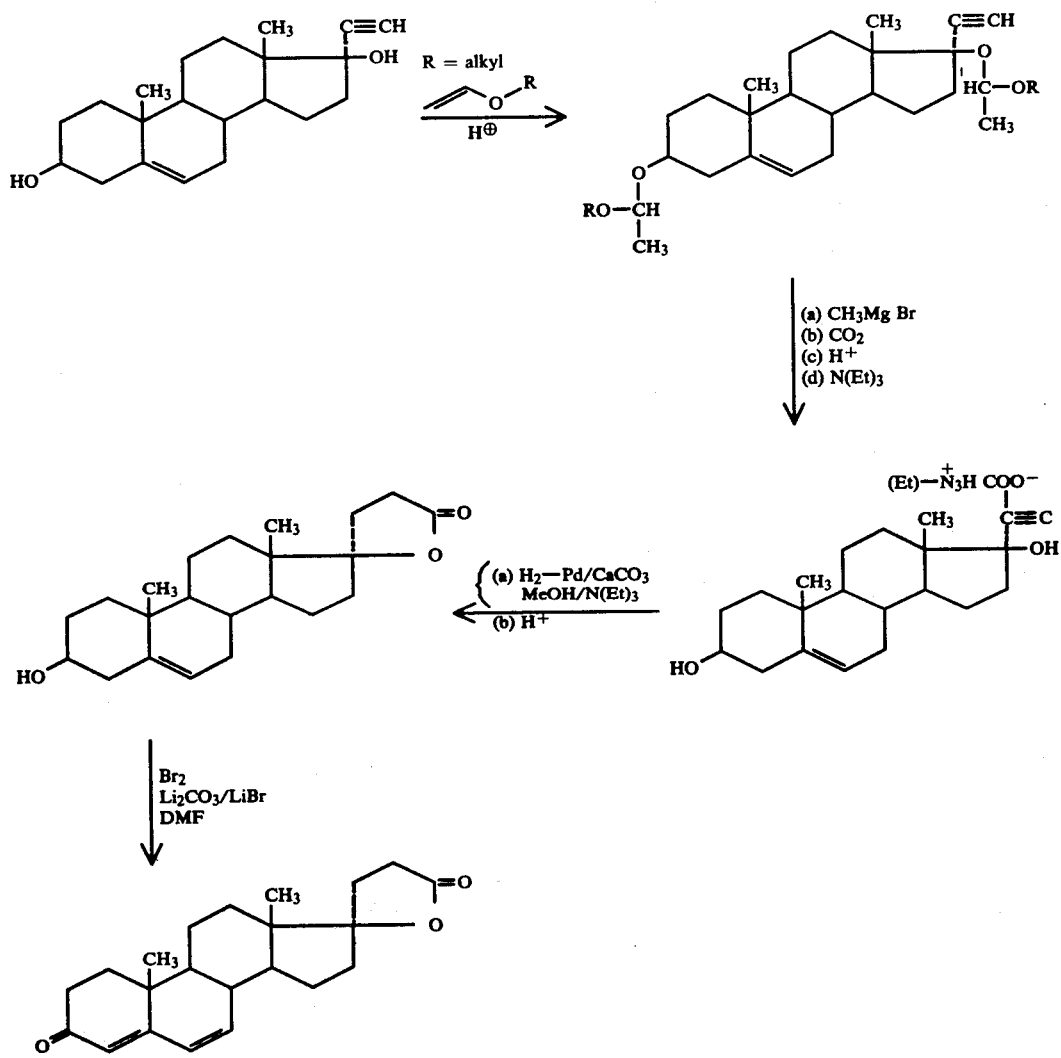
German Offenlegungsschrift No. 2,237,143 describes a method of obtaining the spironolactone according to the following reaction scheme (process C):
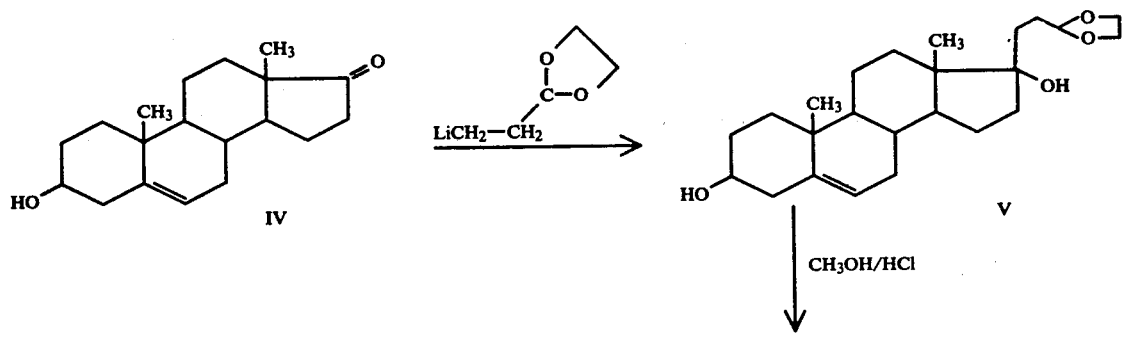

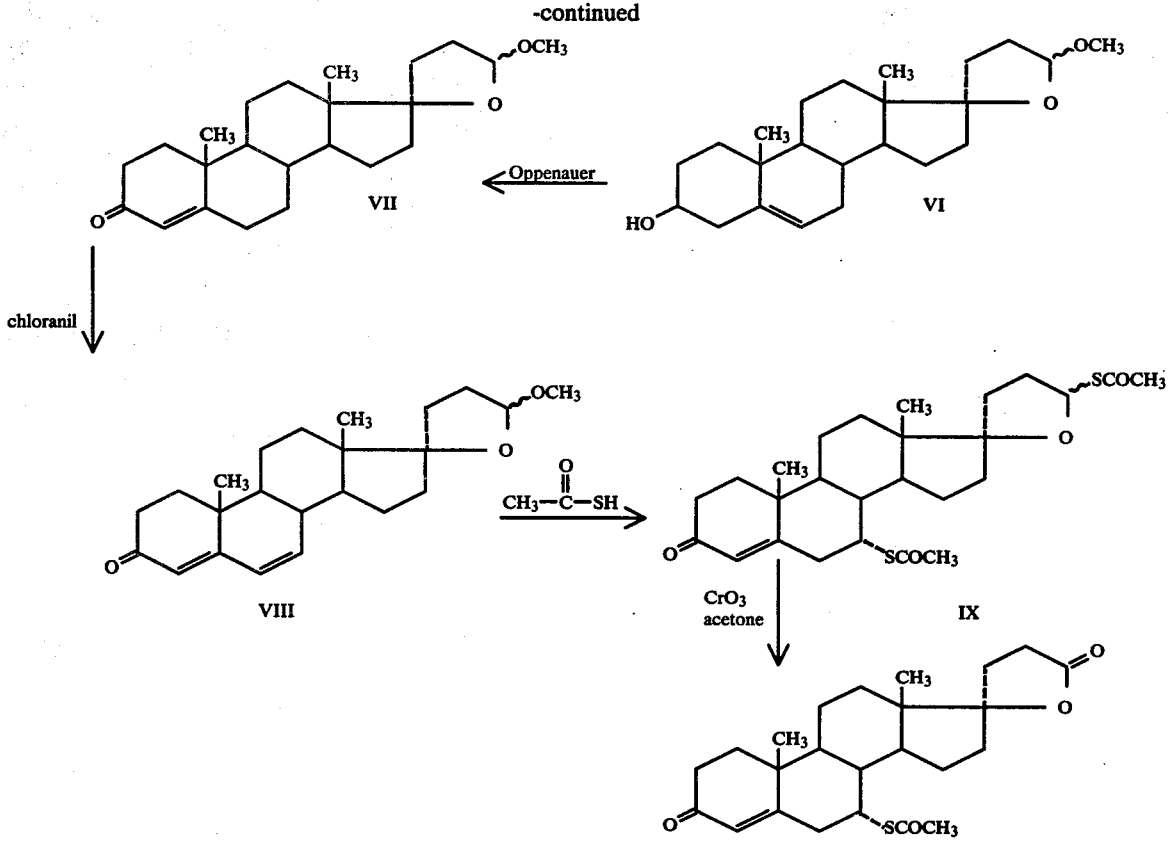

An alternative thereof is claimed in German Offenlegungsschrift No. 2,248,834 (process D) and another in German Offenlegungsschrift No. 2,248,835 (process E).

Finally, German Offenlegungsschrift No. 2,251,476 claims yet another alternative method according to which a start is made from the 3-oxo-4,6-diene derivatives which correspond to the above compounds of the formula V, thioacetic acid is added to these, and the resultant corresponding 3-oxo-7α-acetyl-thio-4-ene derivatives with intact 17β-hydroxy-17α-propionaldehyde-acetal side-chain are oxidised in acid solution to give spironolactone. The addition of thioacetic acid to the 6,7-double bond, while preserving intact the substituents contained in the starting material in 17-position, is described in this patent specification as surprising, since a cyclisation of the following kind

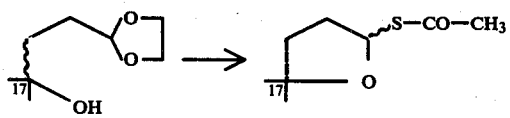

was to be expected in the acid medium of the thioacetic acid.

Experimental verification of this process has now revealed that the 3-oxo-4,6-dienes with 17β-hydroxy-17α-propionaldehyde-acetal side-chain, referred to above as starting materials, are not known at all and also cannot be obtained according to the particulars of DOS No. 2,251,476. For if the 3-oxo-4-enes with 17β-hydroxy-17α-propionaldehyde-acetal side-chain initially obtainable according to DOS Nos. 2,237,143 and 2,248,834 referred to above (cited on page 4 of DOS No. 2,251,476) are dehydrogenated with chloranil (as also, for example, in U.S. Pat. No. 3,137,690, also referred to on page 4 of DOS No. 2,251,476 and on page 12 in the experimental part), then the 4,6-dienes of the cyclic derivatives formed in the above reaction scheme are obtained and not the corresponding 4,6-dienes, and the ether group which derives from the alcohol used as solvent may be present instead of the acetylthio group. The process described and claimed in DOS No. 2,251,476 therefore cannot be performed.

From the operational point of view, all the processes referred to hereinabove for obtaining carboxylic acid lactones of the formula (I) are unsatisfactory. In the first published process A, reactions are used which are little suited to the exigencies of practice, for example the protracted carbon dioxide treatment in the second step and the catalytic hydrogenation in the third.

Process B affords in the subsequent working up a yield of app. 20 percent, referred to the dehydro-epi-androsterone used as starting material for obtaining the 17α-ethinylandrost-5-en-3β,17β-diol indicated as first step in the reaction scheme.

According to the experimental part of the respective patent applications, the yields of processes C to E are between 10 and 23 percent by weight, again referred to the dehydro-epi-androsterone used as starting material.

The present invention provides a process for the manufacture of compounds of the above formula I which affords higher yields than those of the prior art and which from the operational point of view is also simpler, more convenient, and easier to reproduce.

The process of the present invention for the manufacture of compounds of the formula I comprises treating an acetal of 3β,17-dihydroxy-17α-pregn-5-en-21-carboxaldehyde in basic to neutral medium with a brominating agent which is suitable for adding bromine to a double bond, oxidising the 5,6-dibromo derivative obtained with a compound of hexavalent chromium under basic or neutral conditions, dehydrobrominating the product so obtained, and subsequently treating the resultant product with a compound of hexavalent chromium in acid solution, optionally after previous treatment with an acid, or, to introduce the 7α-acylthio group, with the thiocarboxylic acid corresponding to this acylthio group, and, if desired, converting compounds of the formula I, wherein $R_1$ and $R_2$ represent a further 6,7-carbon-carbon bond, into the metal salts of the corresponding 17-hydroxy-21-carboxylic acids in known manner, or converting them in known manner into the compounds of the formula I, wherein $R_1$ represents an acylthio group and $R_2$ represents hydrogen.

The addition of bromine to the 5,6-double bond of the cited starting materials according to the process of this invention can be effected with a brominating agent which is generally able to add bromine to double bonds, while ensuring that the reaction is carried out in basic or neutral medium. This addition can therefore be accomplished in known manner, for example by using bromine in an inert neutral solvent, for example a halogenated hydrocarbon, such as ethylene chloride or chloroform, or in a di-lower alkyl-lower alkanoic amide, for example dimethyl formamide, with or without a buffer, such as an organic or inorganic base, or in an excess of an organic nitrogen base, for example bromine in a tertiary organic aromatic base, such as pyridine or the C-methyl homologs thereof, such as the picolines, in particular collidine. Bromine forms perbromides as intermediates with these nitrogen bases, for example the perbromides of hydrohalogen salts of the bases, for example the perbromides of salts of hydrobromic acid. Such perbromides can also be used with advantage for the bromination according to the invention. In particular, pyridine hydrobromide perbromide is used. It is advantageous to use a small excess over the amount of bromine required in theory for brominating a double bond.

Besides the perbromides of the cited nitrogen bases or of other bases, it is also possible to use the adducts of bromine to ethers, in particular cyclic ethers, such as dioxan. A tertiary aromatic base, such as one of those referred to above, is also advantageously added in these cases.

The perbromides or bromine adducts are reacted in an inert organic solvent, such as one of those referred to above, or also in an ether, a hydrocarbon, in alcohols, in particular lower aliphatic univalent or bivalent alcohols, such as methyl or ethyl alcohol, or n-butanol, or ethylene glycol.

Other bromine addition complexes, besides those mentioned, can also effect the addition, for example the addition complex of bromine and tetramethylammonium bromide.

It is very advantageous to use pyridine hydrobromide perbromide, which is reacted in pyridine solution and at room temperature or at lower or elevated temperature, for example from $-10°$ to $+100°$ C., preferably from $0°$ to $+20°$ C.

The oxidation of the 5,6-dibromo adduct with a compound of hexavalent chromium, for example chromium trioxide or chromic acid, will take place in basic or neutral medium. If appropriate, a sufficient amount of the base used beforehand in the bromination is again added during the oxidation, for example pyridine, so as to avoid overstepping the neutral point, or the bromination reaction mixture obtained in the previous step is treated with a pyridine chromate solution. This operation is advantageously carried out at temperatures of app. $-10°$ to app. $+30°$ C.

The debromination of the chromic acid oxidation product, to be then carried out according to the invention, can also be accomplished in known manner. For this purpose there are used, for example, inorganic basic agents, such as lithium salts, in particular lithium halides, primarily lithium bromide, in the presence of a basic salt of an alkali metal or alkaline earth metal, such as the carbonates or basic carbonates, for example of lithium, sodium, calcium or magnesium. The solvent used in this method is advantageously a dialkylamide of a lower aliphatic carboxylic acid, in particular a di-lower alkyl derivative, for example dimethyl formamide, at temperatures between $0°$ and app. $180°$ C., advantageously at temperatures between $80°$ and $150°$ C. It is also possible to use nitrogen-containing bases of aromatic character for the dehydrobromination, for example those cited hereinabove, especially pyridine or collidine.

After hydrogen bromide has been removed in the manner described, the 4,6-dien-3-one derivative containing the 17α-propionaldehyde-acetal sidechain is obtained as reaction product. This compound can then be processed direct to give the corresponding lactone of the formula (I), wherein $R_1$ and $R_2$ represent a further carbon-carbon bond between position 6 and 7, or indirectly to give compounds of the same type with the 7α-acylthio group. In the first case, the product is oxidised with a compound of hexavalent chromium in acid solution, especially in a mineral acid solution. In doing so, the aldehyde-acetal group is simultaneously deacetalysed, whereupon cyclisation of the propionaldehyde side-chain with the 17β-hydroxyl group, to give the cyclic hemi-acetal and oxidation thereof to give the corresponding lactone group, take place. The oxidation can be carried out with chromium trioxide in acid solution, in particular in sulphuric acid, hydrochloric acid or one of the phosphoric acids, or in a lower carboxylic acid, such as an alkanecarboxylic acid of 1 to 7 carbon atoms, for example formic acid, acetic acid or propionic acid or one of the butyric acids or valeric acids, or in mixtures of these acids, also with or without the addition of water. The oxidation can also be carried out in organic solvents, such as ketones or ethers, for example in acetone, dioxan or tetrahydrofuran, with or without the addition of water.

It is advantageous to carry out a preliminary treatment with one of the cited acids before the oxidation, when the cyclic hemi-acetal is obtained first, and to effect the oxidation in a second step under the conditions just stated.

In the second case, a thioalkane acid is added in known manner to the 4,6-diene derivative obtained in the dehydrobromination step, i.e. as is known for compounds of the formula I, wherein $R_1$ and $R_2$ represent a further carbon-carbon bond between 6- and 7-position, and subsequently or simultaneously, as described above, treated in acid solution with a compound of hexavalent chromium.

The above addition of a thiocarboxylic acid to the 4,6-diene derivative can be carried out in known manner as defined herein, for example by treating the steroid with an excess of thiocarboxylic acid without a solvent at elevated temperature. However, the reaction of the 4,6-steroid diene in a polar solvent, in particular an alcohol, preferably a lower alkanol containing 1 to 7 carbon atoms, with app. 1.5 to 3.5 moles of thiocarboxylic acid, if desired with the addition of water, gives better yields. The best yields are obtained at temperatures between 0° and app. 120° C., for example by carrying out the reaction at the boiling point of the cited alcohols, for example methanol, ethanol, propyl alcohol, isopropyl alcohol, the butanols or pentanols, in the absence of water. The most preferred temperature range is that between 50° and 100° C. In this way very good yields of the desired 7α-acylthio derivative are obtained without any appreciable formation of the 7β-isomer. In particular, lower thioalkanoic acids containing 1 to 7 carbon atoms, such as thioacetic acid, thiopropionic acid or thiovaleric acid, are used as thiocarboxylic acids.

The acetals to be used as starting materials are derived from any aliphatic, alicyclic, araliphatic or mixed aliphatic-alicyclic alcohol, primarily from lower alkanols containing 1 to 7 carbon atoms or lower alkanediols containing 2 to 7 carbon atoms. In particular the ethylene glycol acetal of 3β,17β-dihydroxy-17α-pregn-5-en-21-carboxaldehyde is used as starting material.

The process can be illustrated by the following example of the manufacture of spironolactone or canrenone (3-oxo-17α-pregna-4,6-diene-21,17-carbolactone), wherein the theoretical yields, referred to the starting material I′, are indicated. As is evident, the total yield of spironolactone IV′, referred to the starting material I′, is 47% of theory, and of canrenone V′, 61% of theory:

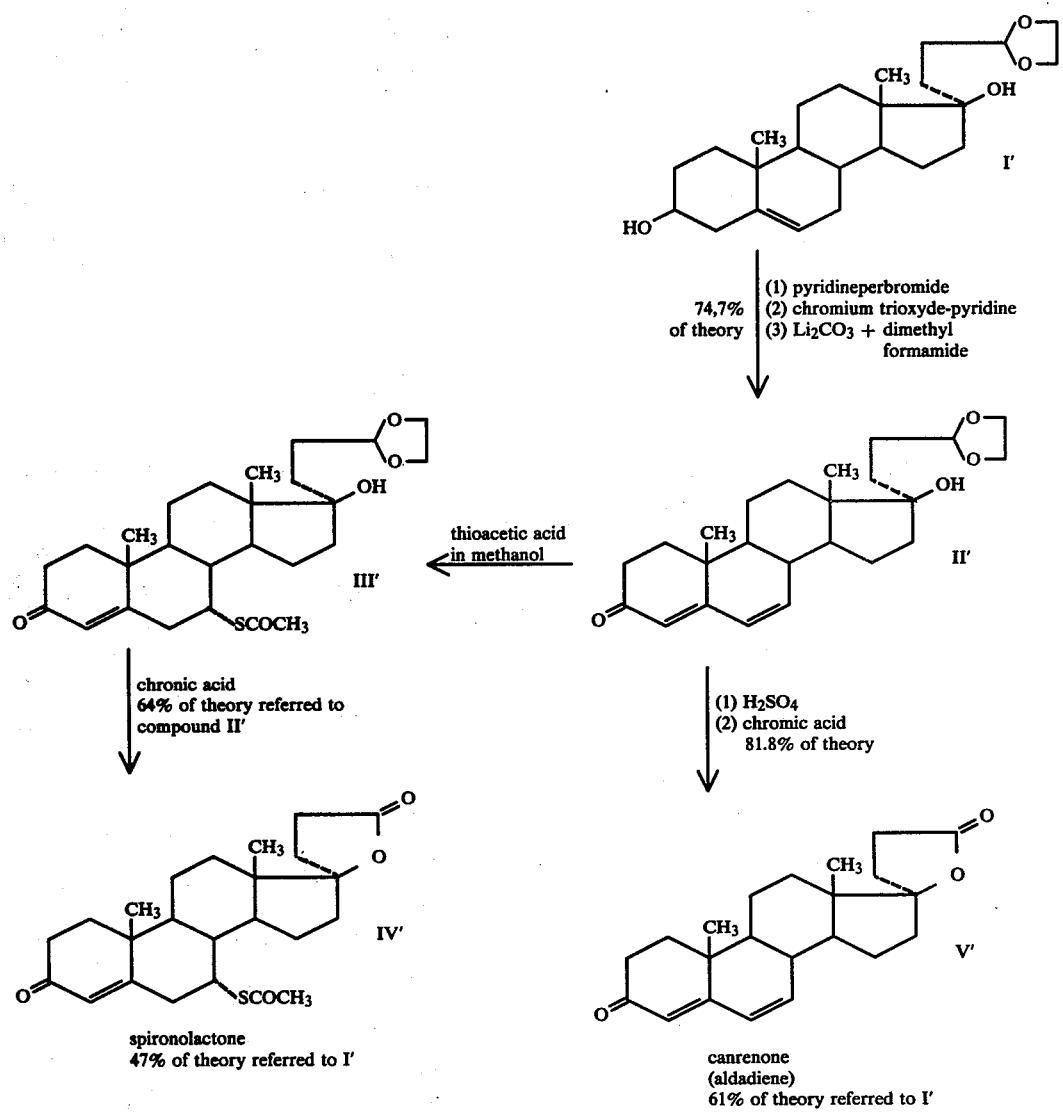

To make a comparison with earlier processes, for example those of the German Offenlegungsschriften cited hereinbefore, the manufacture of I′ from dehydro-epi-androsterone by the method used in these patent specifications of reacting dehydro-epi-androsterone with a chloropropionaldehydeacetal, for example the ethylene acetal, in the presence of lithium, must be included. This reaction affords a yield of app. 60% of the theoretical amount. By converting all yields into percentages by weight, referred to dehydro-epi-androsterone, then in the manufacture of spironolactone by the process of the present invention, for example in Examples 2 and 7, the yield is app. 41 percent by weight, and in the manufacture of canrenone, for example according to Examples 2 and 4, the yield is app. 43 percent by weight. On the other hand, as stated hereinbefore, the yields of the processes C to E are app. 10 to 23 percent by weight of spironolactone, referred to dehydro-epi-androsterone.

The process of the present invention can be carried out with a still higher yield of the desired end products, provided compound I' is obtained from dehydro-epi-androsterone by addition of chloropropionaldehyde-ethylene acetal/Li, by choosing the following novel and inventive modification which, as particular embodiment of the process of the present invention, also forms an object thereof. It has been found that, when reacting the dehydro-epi-androsterone with the chloropropionaldehyde-acetal in the presence of lithium, a substantial amount of dehydro-epi-androsterone can be recovered by reacting the reaction product with steam following the reaction in known manner. Both dehydro-epi-androsterone and the reaction product, for example the 17α-(3'-ethylenedioxy-propyl)-androst-5-en-3β,17-diol, can be readily separated from each other from the component which is not volatile in steam, by means of conventional purification operations, such as chromatography, for example through aluminium oxide, and/or crystallisation. On account of this improvement in obtaining the starting material of the present invention, as illustrated for example in Example 8, it is possible to increase the yield for example of spironolactone, among other things as a consequence of the recovery of starting material, i.e. of dehydro-epi-androsterone, to 50%, and of canrenone to 52%, of the weight of reacted dehydro-epi-androsterone.

A particular advantage of the present process also resides in the fact that in the steps of the reaction of the starting material with the brominating agent, and of the oxidation thereof and the dehydrobromination, the 4,6-dien-3-one intermediate is formed as a unitary compound which can be readily obtained pure, for example by mere crystallisation. As against this, in the processes C to E discussed at the outset, which all proceed via the 4,6-dien-3-one step according to formula VIII, it is difficult to obtain pure preparations of this constitution, since the products are invariably mixtures of alkoxy compounds which are epimeric at the 21a-carbon atom. A consequence thereof is, among other things, that the purification in the final step, for example of the spironolactone, is very tedious and complicated. In contradistinction thereto, products of such quality are obtained in the final steps of the present process that normally a simple purification, for example crystallisation, suffices to obtain entirely pure products.

The advantage of the present process compared with that of process B of U.S. Pat. Nos. 3,738,983 and 3,270,008, besides the advantages already mentioned regarding the yields, also resides in the fact that it involves only a few and technically simple operations.

If desired, the compounds of the formula I, wherein $R_1$ and $R_2$ represent a further carbon-carbon bond between position 6 and 7, can be converted in known manner into the salts, in particular the metal salts, of the corresponding 17β-hydroxy-21-carboxylic acids, for example by treatment with metal hydroxides, such as potassium or sodium hydroxide, in aqueous or alcoholic solution.

If desired, the compounds of the formula I obtained by the process of the present invention, wherein $R_1$ and $R_2$ represent a further carbon-carbon bond in 6,7-position, can be converted in known manner with a thiocarboxylic acid, in particular with a lower thioalkanoic acid, for example one of those referred to hereinbefore, into the compounds of the formula I, in which $R_1$ represents an acylthio group and $R_2$ represents hydrogen.

The invention also comprises those embodiments of the process in which a compound obtained in any intermediate stage is used as starting material and the missing process steps are carried out, or the process is interrupted in any stage, or in which the starting materials are obtained in situ. The invention also has for its object the special embodiment described hereinabove in which the starting material is prepared by reacting dehydro-epi-androsterone with a chloropropionaldehyde-acetal in the presence of lithium, and, following the reaction, the unreacted dehydro-epi-androsterone is recovered after treating the reaction mixture beforehand with steam.

The invention also has for its object the embodiment of the present process in which compounds of the formula I, wherein $R_1$ and $R_2$ represent a further 6,7-carbon-carbon bond, are obtained first and then converted in known manner into the compounds of the formula I, wherein $R_1$ represents an acylthio group and $R_2$ represents hydrogen.

The following Examples serve to illustrate the invention without restricting it to what is described therein.

EXAMPLE 1

20 g of dehydro-epi-androsterone are dissolved in 500 ml of abs. tetrahydrofuran. Then 5.2 g of lithium wire, cut into small pieces, are added. After cooling with an ice bath to 0° C., 38 g of β-chloropropionaldehyde ethylene acetal in 50 ml of abs. tetrahydrofuran are added dropwise with stirring in an atmosphere of nitrogen in the course of 15 minutes. During this addition, the mixture is so intensively cooled (ice/sodium chloride mixture) that the reaction temperature does not exceed 10° C. Stirring is subsequently continued for a further 2½ hours at 0° C. and overnight at room temperature (under nitrogen). Excess pieces of lithium are then separated off and the reaction solution is poured into ice water. Extraction is then performed with ethyl acetate and the extract is washed with saturated aqueous sodium chloride solution until neutral. The crude product obtained after drying the organic phase over $Na_2SO_4$ and evaporating it is filtered through 300 g of neutral $Al_2O_3$ of activity II, unreacted reagent and non-steroid impurities being eluted with 3 liters of petroleum ether/toluene (1:1) mixture. With $CH_2Cl_2$ as eluant, 19.9 g of 17α-(3'-ethylenedioxy-propyl)-androst-5-en-3β,17β-diol are obtained m.p. 181°–182° C. after one recrystallisation from acetone/petroleum ether. Yield: 16.4 g (60.6% of theory).

IR. 3600, 3450 $cm^{-1}(CH_2Cl_2)$.—NMR.: 0.87, s, $CH_3(18)$; 1,02, s, $CH_3(19)$; 3.50, m, CH(3); 3.92, m, —$OCH_2CH_2O$—; 4.91,t, J=4, CH(3'); 5.34, m, CH(6) $(CDCl_3)$.

EXAMPLE 2

To 6 g of 17α-(3'-ethylenedioxy-propyl)-androst-5-en-3β,17β-diol in 60 ml of pyridine are added at 0° C. 5.4 g of solid pyridine hydrobromide perbromide. The mixture is then stirred for 3 hours at 0° C. under anhydrous conditions. One hour after the start of this reaction, 4.5 g of $CrO_3$ in 6 ml of $H_2O$ are added dropwise, with stirring, to 45 ml of ice-cold pyridine, the rate of addition being so chosen that the temperature in the flask does not exceed 10° C. The pyridine chromate solution obtained is then stirred until completion of the parallel bromination reaction at 0° C. The pyridine chromate solution is then poured into the bromination solution and the reaction mixture is stirred initially for a further 3 hours at 0° C. and then additionally overnight at room temperature. The batch is then diluted with a substantial amount of CHCl$_3$ and washed 4 times in succession with saturated aqueous NaCl solution ten times with water. The organic phase is subsequently dried over Na$_2$SO$_4$ and evaporated to dryness in vacuo.

The crude oxidation product is dissolved repeatedly in toluene to remove residual pyridine as an azeotrope and evaporated to dryness in vacuo. The product is dissolved in 108 ml of abs. dimethyl formamide, treated with 10.8 g of LiBr and Li$_2$CO$_3$ respectively, and heated, with stirring, in an atmosphere of nitrogen to 100° C. in the course of 15 minutes and kept at this temperature for a further 1¼ hours. The batch is afterwards allowed to cool, diluted with ethyl acetate, and washed ten times with water and once with saturated sodium chloride solution. The organic phase is dried over Na$_2$SO$_4$, then concentrated in vacuo, and the residue is filtered through 100 g of neutral Al$_2$O$_3$ (activity II). The apolar impurities are first eluted with 500 ml of toluene. The subsequent ethyl acetate eluates consist of 4.56 g of 17β-hydroxy-17α-(3'-ethylenedioxy-propyl)-androsta-4,6-dien-3-one, and melt at 132° C. after one recrystallisation from acetone/petroleum ether. Yield after recrystallisation: 4.44 g (74.7% of theory).

IR.: 3570, 3450, 1655, 1620, 1585 cm$^{-1}$(CH$_2$Cl$_2$).—UV.: 287 (19700) in C$_2$H$_5$OH-.—NMR.: 0.95, s, CH$_3$(18); 1.10, s, CH$_3$(19); ca. 3.95, m, —OCH$_2$CH$_2$O—; 4.89, t, J=4, CH(3'); 5.65, s, CH(4); 6.08, s (2H), CH(6)+CH(7(COCL$_3$).—[α]$_D$= −6° (1.04 in CHCl$_3$).

EXAMPLE 3

5 g of 17β-hydroxy-17α-(3'-ethylenedioxy-propyl)-androsta-4,6-dien-3-one are dissolved at room temperature in 50 ml of methanol. Then 7.5 ml of water and 2.5 ml of thioacetic acid are added in succession and the mixture is stirred for 3 hours at room temperature. The batch is thereafter poured into ice-cold 2 normal aqueous NaHCO$_3$ solution and extraction is performed with ethyl acetate. The extract is washed neutral with saturated aqueous NaCl solution, dried over sodium sulphate and concentrated in vacuo, to yield 5.86 g of 7α-acetylthio-17β-hydroxy-17α-(3'-ethylenedioxypropyl)-androst-4-en-3-one [IR. 3450 (wide) 1685, 1670, 1620 cm$^{-1}$(CH$_2$Cl$_2$); NMR. 0.92, s, CH$_3$(18); 1.22, s, CH$_3$(19); 2.33, s, SCOCH$_3$; 3.94, m, CH(7)+—OCH$_2$CH$_2$O—; 4.91, t, J=4, CH(3'); bs, CH(4) (CDCl$_3$)], which are further processed direct. The 5.86 of crude product are dissolved in 200 ml of acetone and the solution is cooled to 0° C. Then 10 ml of 8 normal CrO$_3$ in 8 normal H$_2$SO$_4$ are added dropwise, with stirring, in such a way that the temperature does not exceed 10° C. The mixture is then stirred for 45 minutes at room temperature. Then 5 ml of the above CrO$_3$ solution are again added dropwise at room temperature and stirring is continued for a further hour at this same temperature. Thereafter 10 ml of methanol are added, and the batch is stirred for 10 minutes and subsequently diluted with ethyl acetate. The ethyl acetate phase is washed 3 times with saturated aqueous solutions of sodium acetate and sodium chloride respectively, dried over Na$_2$SO$_4$ and evaporated to dryness in vacuo. Yield: 5.5 g of a crystalline product from which 2.75 g of spironolactone (7α-acetylthio-3-oxo-17α-pregn-4-en-21,17-carbolactone, 51% of theory, referred to the educt of Example 3), with a double melting point of 135° and 202° C., are obtained by crystallisation from methanol at −10° C. [IR. 1770, 1670–1700 wide, 1620 cm$^{-1}$(CH$_2$Cl$_2$). UV. 240 (19400) in C$_2$H$_5$OH.—NMR. 0,97, s, CH$_3$(18), 1.20, s, CH$_3$(19); 2.31, s, SCOCH$_3$; 2.84, 8-, I$_{6,6}$=15, I$_{6,7}$=4, I$_{4,6}$ 2, CH(6β):3.97, m, CH(7): 5,68, d.I=2. CH(4) (CDCl$_3$).

EXAMPLE 4

1 g of 17β-hydroxy-17α-(3'-ethylenedioxy-propyl)-androsta-4,6-dien-3-one is refluxed with 1 ml of 1 normal aqueous H$_2$SO$_4$ in 90 ml of acetone, with stirring, for 45 minutes. The mixture is then cooled to 0° C. and, with stirring, 7 ml of 8 normal CrO$_3$ in 8 normal aqueous H$_2$SO$_4$ are added dropwise in the course of 15 minutes. The batch is kept for a further 10 minutes at 0° C., then 10 ml of methanol are added. The batch is diluted with ethyl acetate and washed 4 times with saturated aqueous solutions of sodium acetate and sodium chloride respectively. The organic phase is dried over Na$_2$SO$_4$ and evaporated to dryness. The crude product is filtered in CH$_2$Cl$_2$ over Al$_2$O$_3$ (activity II), in the course of which 840 mg of 3-oxo-17α-pregna-4,6-diene-21,17-carbolactone are eluted; m.p. 152°–153° C. after crystallisation from acetone/petroleum ether. Yield: 720 mg (81.8% of theory).

IR.: 1770, 1658, 1620, 1585 cm$^{-1}$ (CH$_2$Cl$_2$).—UV.: 283 (24000) in C$_2$H$_5$OH.—NMR.: 1.00, s, CH$_3$(18); 1.11, s, CH$_3$(19); 5.67, s, CH(4); 6.08, s (2H), CH(6)+CH(7) (CDCl$_3$).

EXAMPLE 5

1 g of 3-oxo-17α-pregna-4,6-diene-21,17-carbolactone are dissolved at room temperature in 6 ml of methanol and to the solution are added in succession 1.5 ml of water and 0.5 ml of thioacetic acid. The mixture is stirred for 3 hours at room temperature and extracted with ethyl acetate. The extract is washed in succession with 2 normal aqueous NaHCO$_3$ solution and with saturated aqueous sodium chloride solution until the neutral point is reached. The organic phase is dried over Na$_2$SO$_4$ and evaporated in vacuo, to yield 1.1 g of crude product from which 550 mg of spironolactone are obtained after crystallisation from methanol at −10° C. A direct comparison reveals this compound to be identical in every respect with the preparation obtained in Example 3.

EXAMPLE 6

3.4 g of 3-oxo-17α-pregna-4,6-diene-21,17-carbolactone are dissolved in 10.2 ml of boiling methanol. Then 2 ml of thioacetic acid are added dropwise to the boiling solution in the course of 5 minutes and the mixture is boiled subsequently for a further 30 minutes, and then cooled to 0° C., whereupon the reaction product crystallises out. The batch is allowed to stand for 15 minutes at −10° C. and the crystals are collected by suction filtration, washed with 10 ml of cold methanol and dried in vacuo at 40° C. Yield: 3.41 g of pure spironolactone with a double melting point of 135° and 202° C. and which by direct comparison, is identical in every respect with the material described in Example 3.

EXAMPLE 7

1.80 g of 17β-hydroxy-17α-(3'-ethylenedioxypropyl)-androsta-4,6-dien-3-one are dissolved in 5.1 ml of boiling methanol. Then 1 ml of thioacetic acid are added dropwise to the boiling solution in the course of 5 minutes and boiling is continued for a further 30 minutes. The batch is thereafter cooled, diluted with ethyl acetate and the ethyl acetate extract is washed in succession with aqueous solutions of NaHCO$_3$ and NaCl until the neutral point is reached. The organic phase is then dried over Na$_2$SO$_4$ and evaporated to dryness in vacuo, to yield 2.09 g of crude product, which is treated in 80 ml of acetone at 0° C., with stirring, with 4 ml of a 8 normal CrO$_3$ solution in 8 normal aqueous H$_2$SO$_4$. The mixture is subsequently stirred for 1 hour at room temperature, treated once more with 2 ml of the above CrO$_3$ solution and stirred for 1 hour. Extraction is effected with ethyl acetate, the extract is washed 3 times with saturated aqueous solutions of sodium acetate and NaCl respectively, dried over Na$_2$SO$_4$, and evaporated in vacuo to dryness. Yield: 1.87 g of crude spironolactone from which 1.25 g of pure compound are obtained after one crystallisation from CH$_2$Cl$_2$-methanol. (Physical data as in Example 3).

EXAMPLE 8

20 g of dehydro-epi-androsterone are dissolved in 500 ml of abs. tetrahydrofuran. Then 5.2 g of clean lithium wire cut into small pieces are added. The mixture is cooled to 0° C. with an ice bath and 38 g of β-chloropropionaldehyde ethylene acetal in 50 ml of abs. tetrahydrofuran are added dropwise, with stirring, in the course of 15 minutes in a nitrogen atmosphere. The reaction mixture is so intensively cooled that the temperature does not rise above 10° C. The mixture is then stirred for a further 2½ hours at 0° C. and overnight at room temperature (in both cases under nitrogen). Excess lithium is then separated off and the mixture poured into ice water. Excess reagent and its degradation products are separated off by steam distillation. The residue, which is non-volatile in steam, is finally extracted with methylene chloride. The methylene chloride phase is washed neutral with saturated aqueous NaCl solution, dried over Na$_2$SO$_4$ and evaporated to dryness in vacuo. The crude product is filtered through 600 g of Al$_2$O$_3$ (activity II) and in doing so 4 fractions are eluted with 1 liter of methylene chloride on each occasion. The column is then washed out with 6 fractions of methylene chloride/ethyl acetate mixture 4:1 (using 1 liter on each occasion). Evaporation of the third fraction yields 3.2 g of unreacted crude dehydro-epi-androsterone from which 2.65 g of pure substance are recovered by crystallisation from acetone/petroleum ether. Fractions 4 to 10 yield 20.1 g of 17α-(3-ethylenedioxy-propyl)-androst-5-en-3β,17β-diol, which melts at 181°-182° C. after crystallisation from methylene chloride/petroleum. (Yield 17 g=74% of theory, taking into account the starting material recovered).

We claim:

1. A process for the manufacture of compounds of the formula

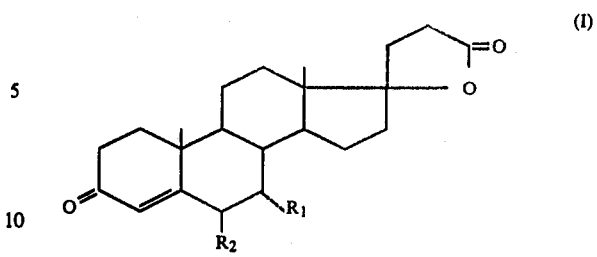

wherein R$_1$ and R$_2$ together represent a further 6,7—C—C bond, which comprises treating an acetal of 3β,17-dihydroxy-17α-pregn-5-en-21-carboxaldehyde in basic or neutral medium with a brominating agent selected from the group consisting of bromine and an organic bromine addition complex, oxidising the acetal of the 5,6-dibromo-3β,17-dihydroxy-17α-pregnan-21-carboxaldehyde obtained with a compound of hexavalent chromium under basic or neutral conditions, at temperatures between about −100 and about +30° C., treating the product so obtained with a member selected from the group consisting of a lithium halide in the presence of a basic alkali metal or alkaline earth metal salt and a nitrogen containing base of aromatic character at temperatures between about 0° and about +180° C., and subsequently treating the resultant acetal of 3-oxo-17β-hydroxy-17α-pregna-4,6-diene-21-carboxaldehyde in seccession or simultaneously with an acid and a compound of hexavalent chromium in acid solution.

2. Process according to claim 1, wherein a resulting acetal of 3-oxo-17β-hydroxy-17α-pregna-4,6-diene-21-carboxaldehyde is treated with a thiocarboxylic acid at temperatures between about 0° and about +120° C., and thereafter with a compound of hexavalent chromium in acid solution, whereby a compound of formula I is obtained, in which R$_1$ represents an α-acylthio group and R$_2$ represents hydrogen.

3. A process according to claim 2 for the manufacture of compounds of formula I wherein an acylthio group R$_1$ is derived from a lower thioalkanoic acid containing 1 to 7 carbon atoms.

4. A process according to claim 2 for the manufacture of compounds of the formula I wherein an acylthio group R$_1$ is the acetylthio group.

5. A process according to claim 2, wherein treatment of any Δ$^{4,6}$-3-oxo-steroid-diene with a thiocarboxylic acid is effected in a lower alkanol containing 1 to 7 carbon atoms using app. 1.5 to 3.5 moles of thiocarboxylic acid and at temperatures between 0° and 120° C.

6. A process according to claim 1, wherein acetals which are derived from lower aliphatic alkanols or alkanediols of 1 to 7 carbon atoms are used as starting materials.

7. A process according to claim 6, wherein the ethylene glycol acetal of 3β,17β-dihydroxy-17α-pregn-5-en-21-carboxaldehyde is used as starting material.

8. A process according to claim 1, wherein a brominating agent selected from the group consisting of
   (a) bromine in a tertiary aromatic nitrogen base and
   (b) a perbromide of a tertiary aromatic nitrogen base or a hydrohalogen salt thereof, or the adducts of bromine to an ether, in a member selected from the group consisting of a lower aliphatic chlorinated hydrocarbon, an ether, a ketone, a di-lower alkyl-lower alkanoic acid amide, a tertiary aromatic amine, and any such solvent in the presence of a buffer, is used.

9. A process according to claim 8(b), wherein pyridine hydrobromide perbromide in pyridine is used as brominating agent and the reaction is carried out at low temperature or at room temperature.

10. A process according to claim 1, wherein the 5,6-dibromo adduct is oxidised with chromium trioxide or with chromic acid in a tertiary aromatic base at temperatures between $-10°$ and app. $+30°$ C.

11. A process according to claim 10, wherein pyridine is used.

12. A process according to claim 1, wherein the dehydrobromination of the chromic acid oxidation product is carried out with inorganic basic agents or with a nitrogen-containing aromatic base.

13. A process according to claim 12, wherein lithium halides in the presence of a basic salt of an alkali metal or alkaline earth metal are used.

14. A process according to claim 13, wherein lithium bromide in the presence of lithium carbonate is used and the dehydrobromination is carried out in a dialkylamide or a lower aliphatic carboxylic acid at temperatures between 80° and 150° C.

15. A process according to claim 1, wherein any 4,6-dien-3-one derivative containing the 17-propionaldehyde acetal side-chain is treated with a compound of hexavalent chromium in a mineral acid solution.

16. A process according to claim 15, wherein the oxidation is carried out with chromium trioxide in sulforic acid in the presence or absence of acetone.

17. A process according to claim 15, wherein the oxidation is carried out with a chromium trioxide in a lower carboxylic acid containing 1 to 7 carbon atoms.

18. A process according to claim 15, wherein a preliminary treatment with an acid selected from the group consisting of a mineral acid and a lower carboxylic acid containing 1 to 7 carbon atoms is carried out before the treatment with a compound of hexavalent chromium in acid solution.

19. A process according to claim 1, wherein the starting materials are prepared by reacting dehydro-epi-androsterone with a chloropropionaldehyde-acetal in the presence of lithium, and the reaction mixture obtained after this reaction is treated with steam and unreacted dehydro-epi-androsterone is recovered from the residue of the steam distillation by crystallisation and/or chromatography.

20. Process according to claim 1, wherein any compound of formula I obtained, wherein $R_1$ and $R_2$ together represent a further 6,7—C—C bond, is treated with a thiocarboxylic acid at temperatures between about 0° and $+120°$ C., whereby a compound of formula I is obtained, wherein $R_1$ represents an α-acylthio group and $R_2$ is hydrogen.

* * * * *